Figure 1:
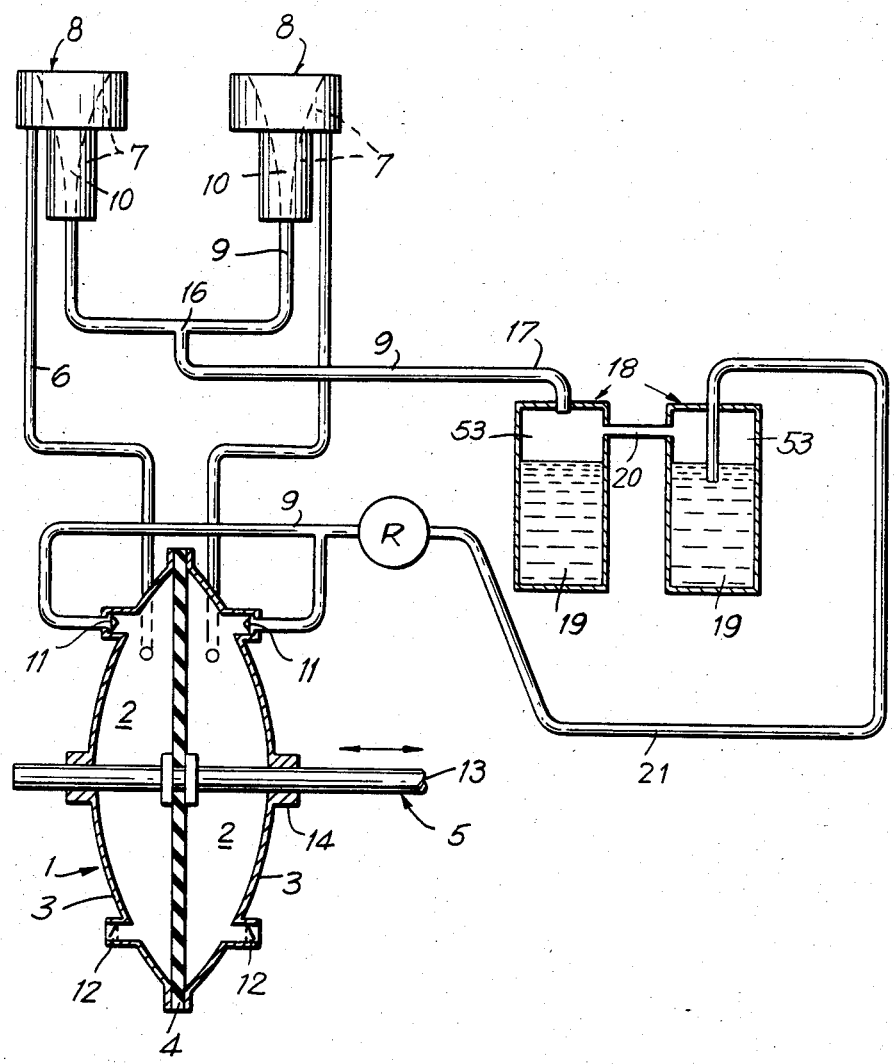

United States Patent [19]

Whittlestone et al.

[11] Patent Number: 4,607,596

[45] Date of Patent: Aug. 26, 1986

[54] MILKING METHODS AND APPARATUS

[76] Inventors: Walter G. Whittlestone, Riverlea Road; Douglas L. Wenham, 90 Braid Road; James D. M. Foreman, 475 River Road, all of Hamilton, New Zealand

[21] Appl. No.: 609,577

[22] Filed: May 11, 1984

[30] Foreign Application Priority Data

May 11, 1983 [NZ] New Zealand .................... 204193

[51] Int. Cl.[4] ........................... A01J 5/04; A01J 5/10
[52] U.S. Cl. ................................ 119/14.02; 119/14.43
[58] Field of Search ................. 119/14.02, 14.4, 14.41, 119/14.42, 14.43, 14.44

[56] References Cited

U.S. PATENT DOCUMENTS

| 1,965,497 | 7/1934 | Johnson | 119/14.42 |
| 2,516,328 | 7/1950 | Lowry | 119/14.43 |
| 2,516,354 | 7/1950 | Taylor | 119/14.43 |

Primary Examiner—Hugh R. Chamblee

[57] ABSTRACT

A milking apparatus utilizing a pumping vessel which provides both vacuum and pulsating pressure to the outer and inner chambers respectively of two chambered breast or teat cups. Milk is taken off via the vacuum connections to the pumping vessel. A method of milking using the apparatus is also described.

7 Claims, 5 Drawing Figures

MILKING METHODS AND APPARATUS

This invention relates to milking apparatus.

Machine milking of humans or animals involves the application of breast or teat cups to the breasts or teats. Modern teat or breast cups are provided with inner milk chambers and outer pulsation chambers and the milking action is derived from pressure changes instigated by a pulsating apparatus communicable with the pulsation (outer) chamber of the breast or teat cups. Pressures in the pulsation chambers of the breast or teat cups vary between atmospheric pressure and a lower pressure (vacuum) and the inner chambers of the cups are subject to a vacuum, usually from the same source as that applied to the pulsation chambers of the cups. The modern milking apparatus incorporates an electric, pneumatic or mechanical pulsator directly communicable with the pulsation chamber of the teat or breast cup whose function it is to sequentially control the application of higher pressure and vacuum to the pulsation chamber of the teat or breast cups. The milking apparatus therefor comprises cups as aforesaid, pulsation means, and means to create a vacuum.

It is an object of the present invention to provide methods of and apparatus for milking animals or humans.

It is a further object of the present invention to provide an apparatus for milking animals or humans which eliminates the need for separate pulsation means.

It is a still further object of the present invention to provide a milking apparatus which is easily cleaned and/or dismantled for cleaning and sterilising.

Further objects and advantages of the present invention will become apparent from the ensuing description which is given by way of example.

Broadly speaking by the present invention there is provided a method of milking using at least one breast or teat cup having outer pulsation chamber and inner milk chamber, said method comprising the steps of applying a breast or teat cup to the breast or teat and applying a pulsating pressure to the pulsation chamber of the breast cup via a vessel communicable with said pulsation and milk chambers of the breast or teat cup, said vessel supplying both vacuum and/or pulsation.

According to a further aspect of the present invention there is provided a method as aforesaid, wherein said vessel is separated by a flexible member into two chambers, each communicable with the inner (milk) and outer pulsation chambers of a set of breast or teat cups wherein the flexible member is continuously reciprocated in said vessel such that vacuum created in the inner milk chambers of each of the breast or teat cups is directly proportional to higher pressure applied to the pulsation chamber of one or other of the said breast or teat cups.

According to a still further aspect of the present invention there is provided a milking apparatus for performing a milking method, said apparatus comprising a vessel having a vessel chamber defined by a rigid part and a flexible part complementary with said rigid part, driving means for reciprocating said flexible part, means for communicably connecting said vessel chamber with the outer pulsation chambers of at least one breast or teat cup, means for communicably connecting said vessel chamber with the inner milk chambers of said at least one breast or teat cup, valving means for controlling the ingress of air from the inner milk chambers of the teat cup into said vessel chamber, and outlet means from said vessel for venting the vessel chamber to atmosphere, the arrangment being such that on reciprocation of said flexible member pulsating pressure can be applied to the pulsation chamber of a breast or teat cup whilst a vacuum is applied in an alternative or simultaneous manner to said inner milk chamber of breast or teat cup.

Figure 2:
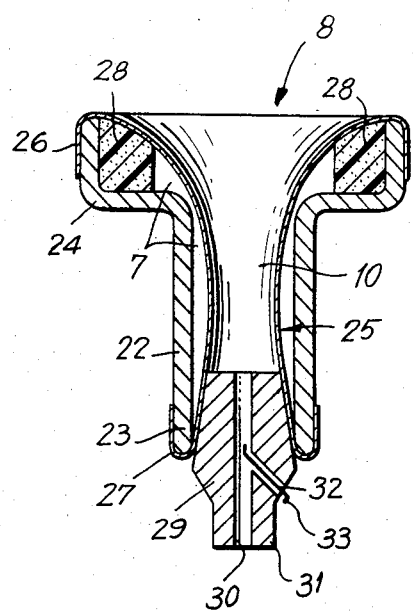
Figure 3:
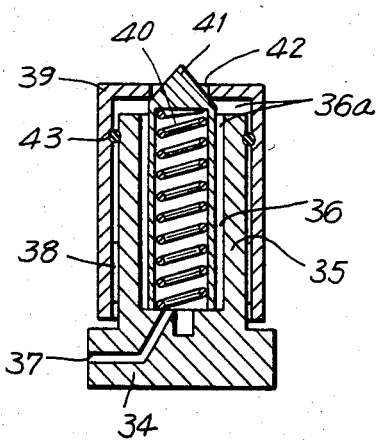
Figure 4:
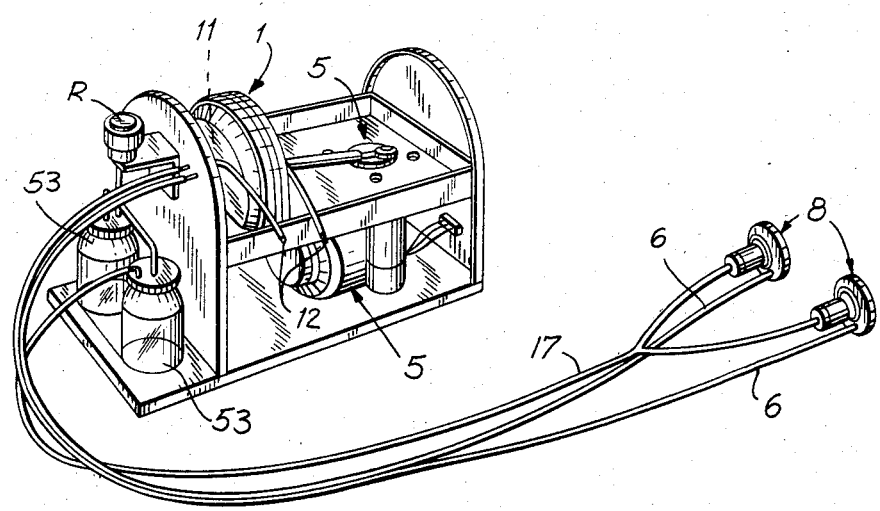
Figure 5:
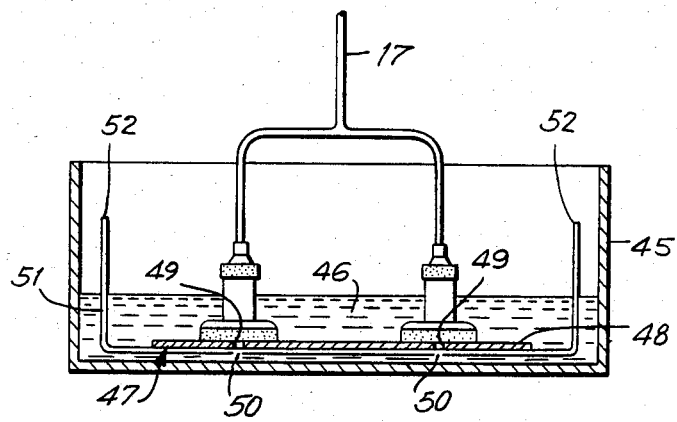

Aspects of the present invention will now be described by way of example only with reference to the accompanying drawings in which:

FIG. 1 is a diagrammatic cross-sectional view of a milking apparatus in accordance with one possible embodiment of the present invention, and FIG. 2 is a diagrammatic cross-section of a breast cup in accordance with one possible embodiment of the present invention, and FIG. 3 is a diagrammatic cross-section of a regulating device for the milking apparatus of FIG. 1, and FIG. 4 is a diagrammatic perspective view of a portable milking apparatus in accordance with the present invention, and FIG. 5 is a diagrammatic cross-section of a breast cup bath in accordance with further aspects of the present invention.

With respect to FIG. 1 of the drawings a milking apparatus for perfoming a milking method in accordance with one possible embodiment of the present invention may comprise a vessel generally indicated by arrow 1 having at least one vessel chamber 2 defined by a rigid part 3 and a complimentary flexible part, generally indicated by arrow 4. Driving means generally indicated by arrow 5 for reciprocating the flexible part 4 are provided. From the vessel 1 a tube 6 connects the vessel chamber 2 with the outer pulsation chamber 7 of a breast cup generally indicated by arrow 8 and means (such as tubes 9) are provided for communicably connecting said vessel chambers 2 with the inner milk chambers 10 of the breast cups 8. The vessel 1 may include valving means 11 for controlling the ingress of air from the inner milk chambers 10 of the breast cups into the vessel chamber 2 and for venting the vessel chamber 2 to atmostphere, via valves 12.

When the driving means 5 is reciprocated the action of the device is such that pulsation pressure can be applied to the pulsation chambers 7 of the breast cups whilst a vacuum is applied in an alternating or simultaneous manner to said inner milk chambers 10 of the breast cups 8.

In the example illustrated by FIG. 1 the vessel 1 is constructed in two halves and has two vessel chambers 2 each being communicable with separate cups of a pair of breast cups 8, and as will be apparent to those skilled in the art, in common usage a pair of breast cups will be used (although the invention is not restricted to the use of a pair of cups and is equally applicable to the use of a single cup only). The vessel 1 illustrated comprises two rigid body parts 3 divided by the flexible member 4 (which can be a rubber diaphragm) connected to the piston 13 of the driving means 5 supported by a bearing 14 as illustrated. The breast cups 8 having individual milk chambers 10 are communicable via flexible tubes 9 including junction 16 and tube 17 to a milk receiving vessel generally indicated by arrow 18. In the example illustrated the milk receiving vessel 18 is in fact two separate milk collecting bottles 19 joined by tube 20 the milk collecting vessel 18 being communciable via the tube 21 with the vessel chambers 2 of the vessel 1 and vacuum regulating device R can be interposed in the tube 21 between the milk collecting vessel and the chambers 2 of the vessel 1.

The valving means 11 are one-way valves and allow air to pass from the milk collecting vessel into the chambers 2 of the vessel 1 whilst the valving means 12 vent the vessel chambers 2 of the vessel 1 to atmosphere, and can be simple flap valves as indicated.

A preferred construction for a breast cup 8 for the apparatus of FIG. 1 is illustrated by FIG. 2 of the drawings. In the example illustrated the breast cup comprises a rigid body 22 having a tubular lower portion 23 and an upper wide integral flange 24, said body 22 accommodating a flexible liner generally indicated by arrow 25 having a downwardly depending flange 26 engageable with the flange 24 and an upwardly depending flange 27 engageable with the lower part of the body 22. Within the flange 24 a compressible annular member 28 is accommodated such being moulded or fabricated from a suitable spongy plastics material of the type which is resistant to moisture. The breast cup assembly is completed by a bung 29 which engages with the lower portion of the body 22 said bung having a milk outlet 30, a nipple 31 to which tube 9 (see FIG. 1) may be attached, and an aperture 32 which accommodates an aperture pin 33. The purpose of the aperture 32 us to allow a controlled amount of air to be induced into the interiors of the breast cup during milk flow and the diameter of the fixed pin 33 relative to the aperture 32 determines the volume of air which can enter the milk chamber 10. The pin 33 ensures that the aperture 32 does not block.

In the assembly illustrated the pulsation chamber 7 for the breast cup is formed between the liner 25 and the body 22 the milk chamber 10 being defined by the interiors of the liner 25 and the bung 29.

The operation of the milking apparatus of the present invention is as follows:

When the driving means drives the diaphragm 4 (see FIG. 1) from right to left valving means 11 on the left hand side closes whilst the valving means 12 opens, and as the diaphragm closes the pulstion chamber of the breast cup to the left is pressurized. In the meantime the valve 11 at the right hand side of the vessel 1 opens and a vacuum is created in tube 21, the milk receiving vessel 18 and the milk chambers 10 of the breast cups, the valving means on the right hand side of the vessel 1 closing off during this phase. When the piston 13 is withdrawn the opposite occurs, in that whilst pressure is increased in the pulsation chamber 7 of the right hand breast cup pressure is being simultaneously reduced in the pulsation chamber 7 of the left hand breast cup, the valves 11 and 12 operating in the manner previously described. Thus a pulsating pressure is applied to the pulsation chamber of the breast cup whilst low pressure (vacuum) is simultaneously applied to the milking chambers 10 of the breast cups, and during the release phase when vacuum exists in the pulsation chambers of the breast cups milk flows from the breast cups into the milk collecting vessel 19. The reciprocation speed of the piston 13 determines pulsation speed, which ideally may be 40 pulsations per minute.

During the operation of the milking apparatus vacuum is applied to the pulsation chambers and/or the milk chambers of the breast cups in proportion to pressure increases in either one of the vessel chambers 2. In other words, vacuum is produced as a "reaction" to a pressure increase.

The vacuum regulating device R in FIG. 1 is shown diagrammatically by FIG. 3 and by way of example, the regulating device may comprise a base 34 mounting a column 35 the column having an internal bore 36 forming an air chamber 36a and an outlet 37 from that air chamber. The column 35 is provided with an external thread 38 which is adapted to be engageable with an internal thread of a regulator cap 39. The aperture 36 is adapted to receive a spring biased valving member 40 which has a conical upper part 41 normally engageable with an inlet aperture 42 of the regulator cap 39. To prevent leakage from the regulator air chamber 36a, an "O"-ring seal 43 can be positioned between the column 35 and the inner walls of the regulator cap 39 as shown. As indicated earlier, the regulator is interposed in the tube 21 (see FIG. 1) and the outlet 37 is therefor communicable with that tube. By adjusting the regulator cap 35 on its screw thread 38 a controlled quantity of air at atmospheric pressure can be introduced into the vacuum to the level which is comfortable for the user. Preferably, spring tension (stiffness) in the spring biased regulator is such that the vacuum in the milking system does not exceed 6" of Mercury (20 K.P.A.), and the maximum allowable movement of cap 39 ensures that adjustment thereof to effect a higher (perhaps unsafe) vacuum cannot be obtained.

One of the problems with conventional milking apparatus where there is no total separation between milk and pulsating air in the system is that sediment mainly as a result of milk vapour tends to build up in parts communicable with the milk and whilst it is a relatively simple matter to wash and sanitise the breast cups and receiving vessel it is not easy to completely wash the system for the purpose of removing sediment from other parts of the equipment. An apparatus in accordance with the present invention can be cleaned using the washing method illustrated with respect to FIG. 5.

As indicated by FIG. 5 of the drawings and the milking apparatus can be washed and cleaned and/or sterilised by the placement of the breast cups 8 in a container 45 filled with a sanitising liquid 46. The cups 8 are mounted on a cup mounting piece generally indicated by arrow 47 within a bath as illustrated said cup mounting piece 47 comprising a flat mounting plate 48 having apertures 49 therein the apertures coinciding with holes 50 in a breather tube 51 which has two ends 52 which extend above the liquid 46 in the bath. For cleaning the milking apparatus is operated in the normal way with the driving means 5 reciprocating the flexible member of the vessel 1 and simulating the milking action. The sanitising fluid 46 from the bath is sucked into the tube 17 not in a stream but in the form of a froth which is as a result of the breathing tube 51 to atmosphere the holes 49 and aperture 50 acting as a mixing device which draws limited amounts of liquid and air into the pipe 17 and mixes both. Thus as the fluid 46 is sucked into the milk collecting vessels 18 in a turbulant state this serves to "scrub" the tubes of the milking apparatus.

After use it would normally be sufficient to stop the wash when the milk collecting vessel 18 is filled near to capacity because the cleaning fluid vapourises during the washing cycle and such froth (particulate milk) is drawn to the chambers 2 of the vessel 1 via the tubes 21 (see FIG. 1) effectively cleaning the interiors thereof without the necessity of completely filling these with the sanitising fluid. Notwithstanding, on some occassions it may be deemed necessary to completely flood the whole system and this can be done by simply continuously supplying the bath with liquid cleaning solution until the whole system is flooded. Because air flows in only one direction through the regulator R there is no need to specifically wash this part of the apparatus although it could obviously be done as the regulator can be easily disassembled.

One of the features of the present invention which will be specially attractive to users is that the vessel 1 can be easily disconnected from the driving means 5 and the milk collecting vessels can be easily disconnected or exchanged. Where the apparatus is a breast milker the milk collecting vessels may be two milk bottles 19 as shown and the tubes 17,26, and 21 can be secured by caps 53 (see FIGS. 1 and 4) which can be secured in their position by a snap-clamp (not shown) as opposed to being secured by a thread.

The driving means 5 for the milking apparatus may comprise a prime mover and reduction box (not shown) which drives cam, crank or eccentric mechanism comprising arm 54 which can be joined to the shaft 13 of the vessel 1 by a releasable pivot mechanism (not shown) again so that the apparatus can be easily dismantled for cleaning or other purposes. The two rigid body parts 3 of the vessel 1 can also be easily dismantled if need be.

The flexible member within the vessel 1 acts as a valving member against the surfaces of the rigid parts of the body of the vessel 1 (which preferably is a curved surface) such that changes in position of the valving member and opening or closing of the valves 11,12 are effected in a gradual manner so that the pulsating and/or vacuum supplied from the apparatus during cycles is not so abrupt as to distress a user of the apparatus.

Pulsation applied to the pulstion chambers of the breast cups in the apparatus illustrated uses both sides of the flexible member 4 and because of this and the action of the valves 12 to obtain a small adjustable sinosodal positive pressure during pulsation, which is acknowledged, enhances stimulation of the breast or teat. The adjustment is simply achieved by adjustments to outlet valves 12 from the vessel.

In the description of a milking apparatus in accordance with one possible embodiment of the present invention the vessel from which pulsation and vacuum are supplied as a diaphragm pump. As will be appreciated by those skilled in the art that equivalents to the vessel described may be found in other displacement apparatus. For example the flexible member may be regarded as being directly equivalent to a reciprocable piston in a piston pump. In a further example the vessel may comprise two vessel chambers each split by a reciprocable displacement member (a diaphragm or a piston) with the pulsation pressure being derived from the vessel chambers direct and the vacuum being derived from the same source via control valves. In each case the apparatus will operate on the same principles. Sequentially the typical operation is as follows:

(a) A piston or diaphragm moves to increase volume of the vessel causing the vacuum in the vessel to rise.

(b) Condition (a) is communicated to the pulsation chamber of the breast or teat cup which on reaching operating vacuum (say 20 KPA) causes the liner to move away from the breast into the milking phase.

(c) Volume displacement in excess of that required to bring about above functions causes inlet valves to the milking system to open so maintaining evacuation of the system.

(d) A second chamber acting out-of-phase with the first chamber provides a complementary pulsation vacuum source and an additional (and identical) source of system vacuum.

As indicated earlier, the milking apparatus illustrated by way of example is a human breast milking apparatus. However, as will be appreciated, should the breast cups 8 be replaced by conventional teat cup assemblies as used for milking animals (such as goats or cows) and the milking vessel 18 was replaced by a milk collection can (not shown) then the milking apparatus is converted into a convenient and portable milker for a farmer. The principles upon which the milking apparatus operates in both cases would be the same.

We claim:

1. A method of milking using a pair of milking cups each having an outer pulsation chamber and an inner milk chamber, said method comprising the steps of causing the pulsation chambers of each of the milking cups to be directly communicable with separate chambers of a pump having at least two pumping chambers separated by a reciprocable member common to both and causing the milk chambers of the milking cups to be communicable each with the two pumping chambers of the pump via a valving means operable to isolate the milk chambers of the milking cups when positive pressure exists in said pump chambers, and reciprocating the reciprocable member so that the vacuum created in the inner milk chambers of each milking cup is directly proportional to high pressure within the pulsation chambers of at least one of the milking cups.

2. A method as claimed in claim 1 including the further step of collecting the milk in a milk container interposed between the milk chambers of the milking cups and the pump.

3. Milking apparatus comprising a vessel having a vessel chamber defined by a rigid member and a flexible member complementary with said rigid member, driving means for reciprocating said flexible member, means for communicably connecting said vessel chamber to the pulsation chamber of at least one milking cup, means for communicably connecting said vesel chamber with the inner milk chambers of the at least one said milking cut, valving means for controlling the ingress of air from the inner milk chambers of the said at least one milking cup into vessel chamber, and outlet means from said vessel for venting the vessel chamber to atmosphere, the arrangement being such that on reciprocation of said flexible member pulsation pressure can be applied to said pulsation chamber of said at least one milking cup whilst a vacuum is applied in one of an alternative and simultaneous manner to said inner milk chamber of said at least one milking cup.

4. Milking apparatus as claimed in claim 3 wherein the vessel has two vessel chambers defined by the flexible member and similar rigid members mounted to either side of the flexible member, each of said vessel chambers being communicable with pulsation and milk chambers of a set of milking cups.

5. Milking apparatus as claimed in claim 4 including milk collecting containers interposed between the vessel chambers and said milking cups.

6. Milking apparatus as claimed in claim 3 wherein the milking cups comprise a rigid body defining a lower chamber and an upper larger chamber, a flexible liner having an upper part with a downwardly depending flange for engaging with the rigid body of the upper larger chamber, an upwardly depending flange engagable with the rigid body of the lower chamber, a compressible annular member accommodated between the flexible liner and the body of the upper larger chamber, and, an outlet bung with a bleed hole to the atmosphere arranged to be accommodated in the lower end of the said milking cup, said milk chamber being defined by the space between the body, the flexible liner and the outlet bung.

7. Milking apparatus as claimed in claim 6 including a vacuum regulating valve interposed between the milk collecting containers and the vessel chambers.

* * * * *